(12) United States Patent
Ho et al.

(10) Patent No.: US 8,927,225 B2
(45) Date of Patent: *Jan. 6, 2015

(54) HUMAN CATECHOL-O-METHYLTRANSFERASE (COMT) ASSAY

(75) Inventors: Shu Leong Ho, Hong Kong (CN); Wing Lok Ho, Hong Kong (CN); David Boyer Ramsden, Worcester (GB)

(73) Assignee: The University of Hong Kong, Hong Kong (CN)

( * ) Notice: Subject to any disclaimer, the term of this patent is extended or adjusted under 35 U.S.C. 154(b) by 1081 days.

This patent is subject to a terminal disclaimer.

(21) Appl. No.: 12/555,529

(22) Filed: Sep. 8, 2009

(65) Prior Publication Data

US 2010/0081147 A1    Apr. 1, 2010

Related U.S. Application Data

(60) Provisional application No. 61/100,576, filed on Sep. 26, 2008.

(51) Int. Cl.
| | |
|---|---|
| *C07K 7/08* | (2006.01) |
| *C07K 16/44* | (2006.01) |
| *G01N 33/535* | (2006.01) |
| *G01N 33/543* | (2006.01) |
| *G01N 33/573* | (2006.01) |
| *C07K 16/40* | (2006.01) |
| *C12N 9/10* | (2006.01) |

(52) U.S. Cl.
CPC .............. *C07K 16/44* (2013.01); *C12N 9/1011* (2013.01); *C07K 2319/40* (2013.01); *C07K 16/40* (2013.01); *G01N 33/573* (2013.01); *C12Y 201/01006* (2013.01); *G01N 2333/91022* (2013.01); *C07K 7/08* (2013.01); *Y10S 435/975* (2013.01)
USPC ......... 435/7.4; 435/7.93; 435/7.94; 435/7.95; 435/15; 435/69.3; 435/69.7; 435/975; 436/501; 436/518; 436/528; 436/547; 436/548; 530/300; 530/324; 530/326; 530/350; 530/387.9; 530/388.26; 530/389.1; 530/391.1; 530/391.3; 530/403

(58) Field of Classification Search
CPC . G01N 33/535; G01N 33/543; G01N 33/573; G01N 2333/91022; C07K 7/08; C07K 16/40; C07K 16/44; C07K 2319/40; C12N 9/1011; C12Y 201/01006
USPC ................ 435/7.4, 7.93, 7.94, 7.95, 15, 69.3, 435/69.7, 975; 436/501, 518, 528, 547, 436/548, 819; 530/300, 324, 326, 350, 530/387.9, 388.26, 388.9, 389.1, 389.9, 530/391.1, 403, 391.3
See application file for complete search history.

(56) References Cited

U.S. PATENT DOCUMENTS

| | | | | |
|---|---|---|---|---|
| 5,863,734 | A * | 1/1999 | Karayiorgou et al. ........ | 435/6.12 |
| 6,518,011 | B1 * | 2/2003 | Seiffert et al. .................... | 435/4 |
| 7,846,746 | B2 * | 12/2010 | Nollau et al. ................. | 436/518 |
| 7,943,345 | B2 * | 5/2011 | Park et al. .................... | 435/69.7 |
| 2005/0255504 | A1 * | 11/2005 | Parl ................................... | 435/6 |

FOREIGN PATENT DOCUMENTS

WO          91/11513       *  8/1991

OTHER PUBLICATIONS

Harlow et al., 1988. Antibodies. A Laboratory Manual, Cold Spring Harbor Laboratory, Cold Spring Harbor. pp. 554-612.*
Cardozo et al., 2005. Analyte peptidomimetics selected from phage display peptide libraries: a systematic strategy for the development of environmental immunoassays. Environmental Science & Technology 39: 4234-4241.*
Brizzard, 2008. Epitope tagging. BioTechniques 44: 693-695.*
Ho, P.W.L., et al., "Effects of Plasticisers and Related Compounds on the Expression of the Soluble Form of Catechol-O-Methyltransferase in MCF-7 Cells," Current Drug Metabolism, 2008, 9:276-279.
Ho, P.W.L., et al., "Estrogenic Phenol and Catechol Metabolites of PCBs Modulate Catechol-O-Methyltransferase Expression via the Estrogen Receptor: Potential Contribution to Cancer Risk," Current Drug Metabolism, 2008, 9:304-309.
Jiang, H., et al., "Human Catechol-O-Methyltransferase Down-Regulation by Estradiol," Europharmacology, 2003, 45:1011-1018.
Xie, T., et al., "Characterization and Implications of Estrogenic Down-Regulation of Human Catechol-O-Methyltransferase Gene Transcription," Molecular Pharmacology, 1999, 56:31-38.

* cited by examiner

*Primary Examiner* — Gail R Gabel
*Assistant Examiner* — James L Grun
(74) *Attorney, Agent, or Firm* — Saliwanchik, Lloyd & Eisenschenk

(57) ABSTRACT

Disclosed is an assay (method) to quantify the amounts of catecholamine-O-methyltransferase (COMT) protein in samples, such as extracts from cell cultures, body fluids, tissues, and environmental samples. It uses novel agents (anti-NE, COMT-NE, or COMT-epitope-NE) in combination with two previously described agents (anti-COMT and COMT) in a competitive ELISA system to achieve this aim.

13 Claims, 11 Drawing Sheets
(6 of 11 Drawing Sheet(s) Filed in Color)

List of 10 hydrophilic amino acids
in NE sequence:

Threonine (Thr)     Serine (Ser)
Aspartate (Asp)     Asparagine (Asn)
Glutamate (Glu)     Glutamine (Gln)
Arginine (Arg)      Lysine (Lys)
Tyrosine (Tyr)      Proline (Pro)

Secondary structure prediction of NE:

Alpha helix: 0%        Beta turn: 0%
$3_{10}$ helix: 0%     Bend region: 0%
Pi helix: 0%           Random coil: 100%
Beta bridge: 0%        Ambigous states: 0%
Extended strand: 0%    Other states: 0%

FIG. 4

293-COMT-NE: positive control lysate from HEK293 cells overexpressing COMT-NE
GST-MB-COMT-NE: Purified recombinant GST-MB-COMT-NE protein from E. Coli.

NE: TKENPRSNQEESYDDNES
B4: TKENPRTNQEESYDDNES : Ser (S) → Thr (T))
B5: TKENPRSNQDESYDDNES : Glutamate (E) → Aspartate (D)
B6: TKENPRSNQPPSYDDNES : 2Glutamate (EE) → 2Proline (PP)

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

| Standards | Abs (405nm) | |
|---|---|---|
| Blank | 0.162 | 0.168 |
| No Standard | 0.924 | 0.888 |
| 80mg/ml | 0.312 | 0.288 |
| 40mg/ml | 0.390 | 0.372 |
| 20mg/ml | 0.528 | 0.522 |
| 10mg/ml | 0.654 | 0.594 |
| 5mg/ml | 0.774 | 0.762 |
| 2.5mg/ml | 0.834 | 0.810 |

| Samples (total protein) | Abs (405nm) | | | |
|---|---|---|---|---|
| Sample #1 (200mg) | 0.828 | 0.780 | 0.786 | 0.744 |
| Sample #2 (100mg) | 0.840 | 0.882 | 0.810 | 0.858 |
| Sample #3 (50mg) | 0.882 | 0.864 | 0.912 | 0.924 |
| Sample #4 (25mg) | 0.900 | 0.882 | 0.906 | 0.900 |

○ STD (Standard: Concentration vs MeanValue)

$y = (A - D)/(1 + (x/C)^B)) + D$:

| A | B | C | D | R2 |
|---|---|---|---|---|
| 0.906 | 1.099 | 16.347 | 0.193 | 0.997 |

Concentration (S-COMT-FLAG, µg/ml)

```
                        SEQUENCE LISTING

<160> NUMBER OF SEQ ID NOS: 10

<210> SEQ ID NO 1
<211> LENGTH: 18
<212> TYPE: PRT
<213> ORGANISM: Artificial sequence
<220> FEATURE:
<223> OTHER INFORMATION: synthetic, not related to any organism

<400> SEQUENCE: 1

Thr Lys Glu Asn Pro Arg Ser Asn Gln Glu Glu Ser Tyr Asp Asp Asn
1               5                   10                  15

Glu Ser

<210> SEQ ID NO 2
<211> LENGTH: 39
<212> TYPE: DNA
<213> ORGANISM: Homo sapiens

<400> SEQUENCE: 2
cgcggatccg ccaccatggg tgacaccaag gagcagcgc                            39

<210> SEQ ID NO 3
<211> LENGTH: 37
<212> TYPE: DNA
<213> ORGANISM: Homo sapiens

<400> SEQUENCE: 3
cgcggatccg ccaccatgcc ggaggccccg cctctgc                              37

<210> SEQ ID NO 4
<211> LENGTH: 89
<212> TYPE: DNA
<213> ORGANISM: Homo sapiens
<220> FEATURE:
<221> NAME/KEY: misc_feature
<223> OTHER INFORMATION: synthetic (chimeric sequence)

<400> SEQUENCE: 4
ctggaattct cagctttcgt tatcatcata gctttcttcc tggttgctac gcgggttttc      60
tttggtgggc cctgcttcgc tgcctgggc                                       89

<210> SEQ ID NO 5
<211> LENGTH: 30
<212> TYPE: DNA
<213> ORGANISM: Homo sapiens
<220> FEATURE:
<221> NAME/KEY: misc_feature
<223> OTHER INFORMATION: synthetic (chimeric sequence)

<400> SEQUENCE: 5
cgcggatcca gcgtgctgga ggccattgac                                      30
```

```
<210> SEQ ID NO 6
<211> LENGTH: 90
<212> TYPE: DNA
<213> ORGANISM: Homo sapiens

<400> SEQUENCE: 6
ctggaattct cagctttcgt tatcatcata gctttcttcc tggttgctac gcgggttttc      60
tttggtaatc acggcgtcca cgatcttgcc                                      90

<210> SEQ ID NO 7
<211> LENGTH: 19
<212> TYPE: PRT
<213> ORGANISM: Homo sapiens
<220> FEATURE:
<221> NAME/KEY: MISC_FEATURE
<223> OTHER INFORMATION: synthetic (chimeric sequence)

<400> SEQUENCE: 7

Asp Thr Tyr Cys Glu Gln Lys Glu Trp Ala Met Asn Val Gly Asp Lys
1               5                   10                  15

Lys Gly Lys

<210> SEQ ID NO 8
<211> LENGTH: 18
<212> TYPE: PRT
<213> ORGANISM: Artificial sequence
<220> FEATURE:
<223> OTHER INFORMATION: synthetic, not related to any organism
<220> FEATURE:
<221> NAME/KEY: MISC_FEATURE
<223> OTHER INFORMATION: synthetic (chimeric sequence)

<400> SEQUENCE: 8

Thr Lys Glu Asn Pro Arg Thr Asn Gln Glu Gly Ser Tyr Asp Asp Asn
1               5                   10                  15

Glu Ser

<210> SEQ ID NO 9
<211> LENGTH: 18
<212> TYPE: PRT
<213> ORGANISM: Artificial sequence
<220> FEATURE:
<223> OTHER INFORMATION: synthetic, not related to any organism
<220> FEATURE:
<221> NAME/KEY: MISC_FEATURE
<223> OTHER INFORMATION: synthetic (chimeric feature)

<400> SEQUENCE: 9

Thr Lys Glu Asn Pro Arg Ser Asn Gln Asp Glu Ser Tyr Asp Asp Asn
1               5                   10                  15

Glu Ser

<210> SEQ ID NO 10
<211> LENGTH: 18
<212> TYPE: PRT
<213> ORGANISM: Artificial sequence
<220> FEATURE:
<223> OTHER INFORMATION: synthetic, not related to any organism

<400> SEQUENCE: 10

Thr Lys Glu Asn Pro Arg Ser Asn Gln Pro Pro Ser Tyr Asp Asp Asn
1               5                   10                  15

Glu Ser
```

HUMAN CATECHOL-O-METHYLTRANSFERASE (COMT) ASSAY

CROSS-REFERENCE TO RELATED APPLICATION

The subject application claims the benefit of U.S. Provisional Application Ser. No. 61/100,576, filed Sep. 26, 2008, which is incorporated herein by reference in its entirety.

BACKGROUND OF INVENTION

COMT is an enzyme which is present in many tissues in the human body. Its primary function is to inactivate and thus facilitate the removal from the body of adrenaline, noradrenaline and dopamine (catecholamines), which act as hormones and neurotransmitters. The present inventors have shown previously that the cellular levels of the enzyme are regulated by the female hormone, estradiol. Many chemicals, both manmade and naturally occurring, can mimic or inhibit the actions of estradiol. If introduced in humans, such chemicals may cause disruption of the normal actions of estradiol and cause health problems at all stages of human life. These chemicals, together with others that affect the actions and metabolism of other hormones, are called collectively endocrine disruptors. Chemicals which affect estradiol actions are probably the most important class of endocrine disruptors. They have been associated with falling sperm counts in Western males, and in the causation of common cancers such as breast cancer and ovarian cancer.

The present inventors have shown that polychlorinated biphenyls (PCBs; universally recognized as posing very serious threats to human health and the wider environment) and a variety of plasticisers and related chemicals are able to modulate levels of COMT protein expression. None of these chemicals is closely related to estradiol, but nevertheless they modulate levels of COMT via the same mechanism as estradiol (Ho et al., 2008a,b). Thus, an assay of COMT protein in cells exposed to such a chemical is a measure of the estrogenic activity of the chemical. Large numbers of chemicals present in, or potentially to be introduced into, the environment have never been assessed for their endocrine disrupting estrogenic potential. This is because the two-generation rat test, which is the recognized test for endocrine disruption, is very time-consuming and extremely expensive. Legislation enacted by the European Union indicates that there are approximately 30,000 chemicals which must be tested. As stated above, assay of COMT protein potentially provides a measure of estrogenic endocrine disrupting potential. Current methods of assaying COMT protein are slow, labor-intensive and limited in sample handling capacity. For example, current assay of human COMT protein concentration is accomplished by use of polyacrylamide electrophoretic (SDS-PAGE)/Western blotting assays. SDS-PAGE involves the use of buffers and gels containing acrylamide and bisacrylamide, which are neurotoxic, and sodium dodecyl sulphate which is a lung irritant and sensitizer. Although many laboratories use commercially available pre-cast gels and prepared buffers to minimize staff exposure to these chemicals, they are, nevertheless, within the laboratory environment and require appropriate safety procedures to be carried out to ensure safe handling and disposal. SDS-PAGE/Western blotting is time-consuming, laborious, difficult to quantify accurately, relatively limited in its capacity for processing samples and consequently is expensive.

An alternative method of estimation COMT concentration is to assay COMT activity and extrapolate the results. This involves use of radioactive substrates for the enzyme, with their attendant hazards and problems of disposal of contaminated materials. Accordingly, there is a need for a COMT assay that is simple, inexpensive, and can handle many samples. The assay described below addresses these problems, because it is simple to use, inexpensive, and has a high sample handling capacity. Thus, it is particularly well-suited as an initial screening system for potential estrogenic endocrine disrupters.

BRIEF SUMMARY

The invention provides a simple, accurate, inexpensive, and rapid method for assaying COMT protein levels in biological cultures, tissues, fluids, and environmental samples.

Other aspects of the invention are novel antibodies, polypeptides, and polynucleotides. In still other aspects, the invention provides kits comprising materials useful for assays.

BRIEF DESCRIPTION OF DRAWINGS

The file of this patent contains at least one drawing executed in color. Copies of this patent with color drawings will be provided by the Patent and Trademark Office upon request and payment of the necessary fee.

FIG. 4 provides the predicted secondary structure of Novel Epitope (NE).

BRIEF DESCRIPTION OF SEQUENCES

Figure 1:
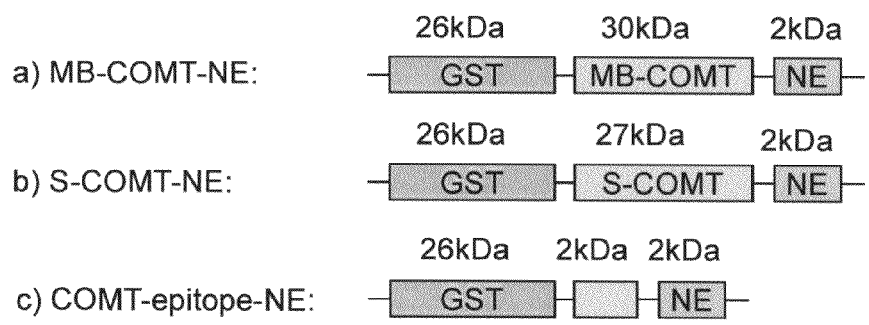
FIG. 1 depicts the linear structure of Novel Epitope (NE) constructs.

SEQ ID NO: 1 is the 18 amino acid Novel Epitope (NE).

SEQ ID NO: 2 is a forward primer for human S-COMT cDNA containing a BamHI restriction site.

SEQ ID NO: 3 is a forward primer for human MB-COMT cDNA containing a BamHI restriction site.

SEQ ID NO: 4 is a reverse primer for S- and MB-COMT encoding the NE sequence and an EcoRI restriction site.

SEQ ID NO: 5 is a forward primer for COMT-epitope containing a BamHI restriction site.

SEQ ID NO: 6 is a reverse primer for COMT-epitope and encoding the NE sequence and an EcoRI restriction site.

SEQ ID NO: 7 is residues 80-98 of human COMT, which is common to both the MB- and S-isoforms.

SEQ ID NO: 8 is the variant #1 of 18 amino acid Novel Epitope (NE).

SEQ ID NO: 9 is the variant #2 of 18 amino acid Novel Epitope (NE).

SEQ ID NO: 10 is the variant #3 of 18 amino acid Novel Epitope (NE).

DETAILED DISCLOSURE

COMT is a ubiquitous enzyme that catalyzes the transfer of the methyl group from the coenzyme S-adenosyl-L-methionine (SAM) to one of the hydroxyl groups of catechols in the presence of magnesium (Mg). Its normal physiological role is the methylation of catecholamines such as the endocrine, neurotransmitter and hypertensive agents, dopamine, noradrenaline and adrenaline as part of the catabolism of these compounds. Previously, the present inventors identified that the transcription of the COMT gene in humans is powerfully regulated by estradiol in a non-classical manner but involving the estradiol alpha-receptor (Xie et al., 1999; Jiang et al., 2003). COMT may play an important role in the pathophysiology of different human disorders including estrogen-induced cancers, Parkinson's disease, depression, schizophrenia, and hypertension (Bonifácio et al., 2007; Tom et al., 1998; Lewandowski, 2007; Houston, 2007). This is because the COMT methylates other substrates such as catechol estrogens (e.g., carcinogenic 4-hydroxyestradiol), indolic intermediates in melanin metabolism, xenobiotic catechols (e.g., carcinogenic flavonoids), and drugs (e.g., levodopa).

Also, the expression of COMT is not only influenced by estradiol but also by compounds of widely different chemical structure but which have the capacity to either mimic or antagonize the actions of estradiol. In this category are compounds such as polychlorinated biphenyls (PCBs) and plasticizers such as bis isohexyl phthalate and related compounds such as octylphenol (Ho et al., 2008a, b). In addition, it should be noted that the regulation of transcription of human genes is often complex and that other non-estrogenic agents may well be capable of modulating transcription of the COMT gene via other direct and indirect pathways. Altered COMT activities are found in different physiological states both in animals and humans. COMT may play an etiologic role in tumor formation (Ho et al., 2008a,b; Thompson et al., 2000).

This assay can be used to measure human COMT protein concentrations in extracts from various tissues and cells, and body fluids. Because various COMT inducers and inhibitors such as xenoestrogens and existing drugs (e.g., Entacapone and Tolcapone used in the treatment of Parkinson's disease), and drugs which affect COMT expression as an adverse event, can affect COMT expression, this assay can be used to assess the effects of such compounds. As mentioned above, a variety of compounds such as PCBs, plasticizers and xenoestrogens, which are present as environmental pollutants, affect COMT expression (Ho et al., 2008a,b). Thus this assay can also be used to assess the effects of such compounds. In addition, the growing concern of environmentalists over the effects of industrial pollutants has led to the European Union to pass legislation, coming into effect in 2008 (REACH Programme), requiring manufacturers to assay the endocrine disrupting effects of chemicals used in their processes. Currently, the list stands at approximately 30,000 chemicals. A COMT assay in conjunction with a human cell-line which expresses both COMT and the estradiol receptor (e.g., MCF-7 cells) would provide a cheap initial screen of estrogenic activity.

The present inventors' research has involved the assay of COMT and detailed investigation of the regulation of the human COMT gene (Xie et al., 1999; Jiang et al., 2003) in relation to elucidating factors involved in the etiology of idiopathic Parkinson's disease in an attempt to explain the slight male cf. female bias in the incidence of the disease. This has led to the recognition of the possibility of using COMT assays to assess endocrine disruptor potential (Ho et al., 2008a,b).

The ELISA of the subject invention is simple to use. It has high degrees of specificity and sensitivity, low intra- and inter-assay coefficients of variation, and uses chemicals that pose a low risk to human health and are easily disposed of. Thus, it has a low cost to benefit ratio. It is flexible in its sample handling and can be used to process either low or high numbers of samples.

It makes available for the first time the ability to measure human COMT protein expression in a large number of samples at a low cost and with simplicity and accuracy.

Figure 2:
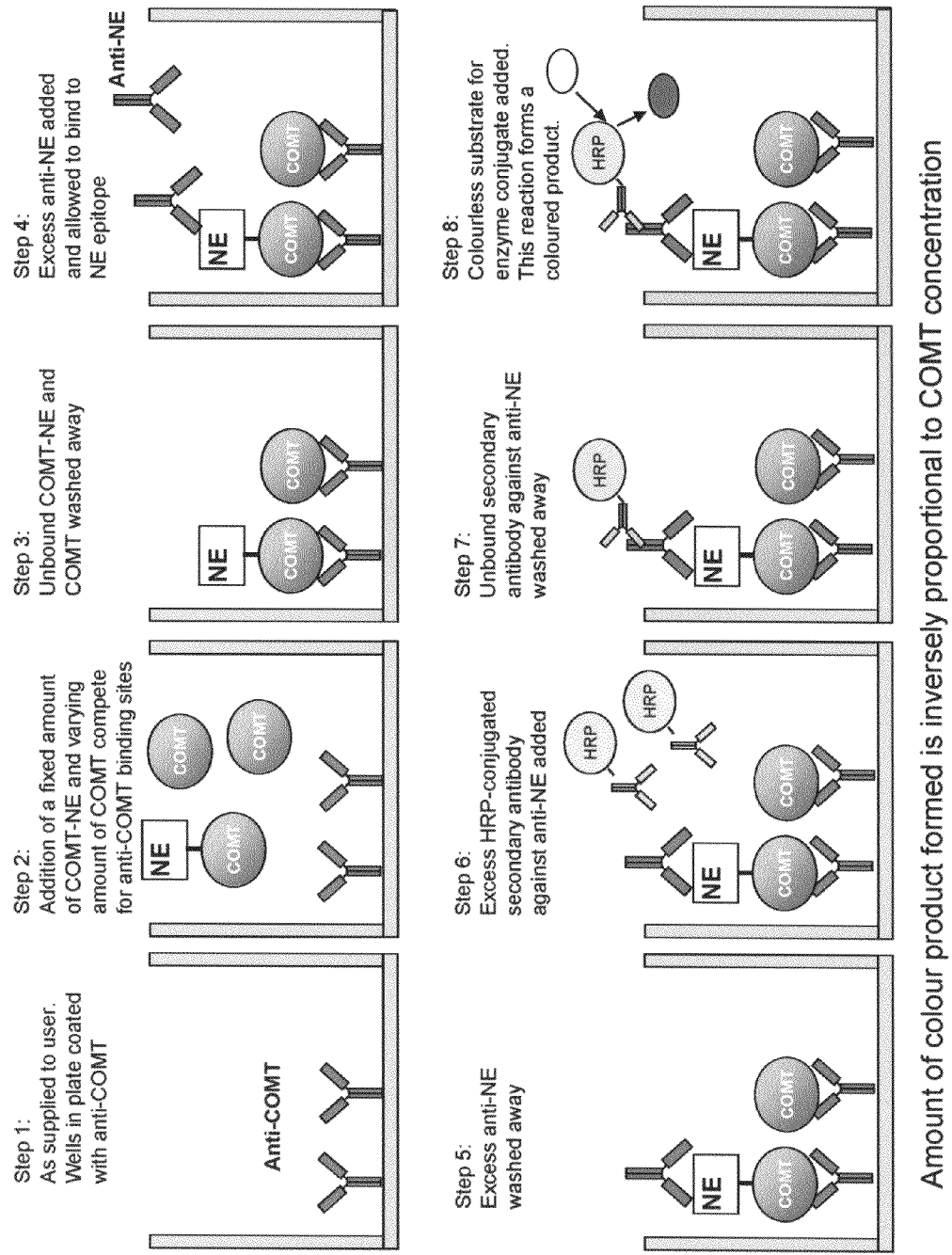
FIG. 2 illustrates how an embodiment of the COMT assay can be carried out.
Figure 3:
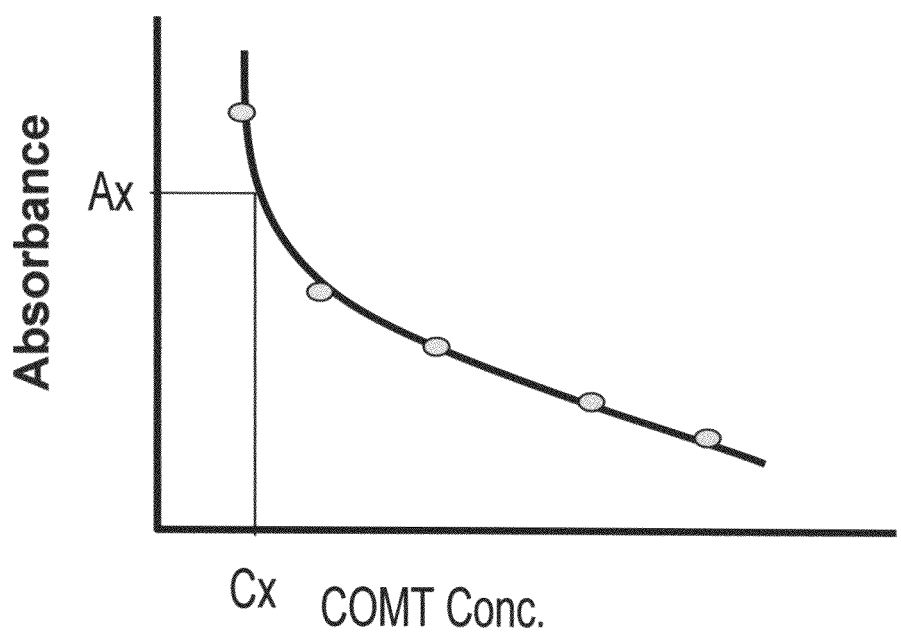
FIG. 3 graphically depicts how an embodiment of the COMT assay works. Color intensity in this assay is inversely proportional to COMT concentration in the standard and in samples of unknown concentration.

A novel 18-amino acid peptide sequence (Novel Epitope, NE) possessing no homology (<30%) to any human proteins (FIG. 1) was designed and cloned into native COMT as a tag for protein detection in this invention. An example of how the assay works is shown in FIGS. 2 and 3. Two antibodies (anti-COMT and anti-NE), one of which is unique (anti-NE) and two proteins (COMT and COMT-NE), one of which is unique (COMT-NE), have been produced. An alternative to using COMT-NE is to use COMT-epitope-NE. Various chemicals for washing and color formation and a third antibody (e.g. HRP-conjugated anti-IgG) with an enzyme conjugated to the antibody can be purchased from any number of suppliers. These are commonly available. A preferred embodiment of the assay can use a plastic 96-well plate in which the wells are coated with a predetermined fixed amount of anti-COMT bound to the bottom of each well. In eight of the wells predetermined fixed amounts of COMT and a fixed amount of COMT-NE are added so that a standard curve may be generated from the results obtained from these wells. In the remaining wells a fixed amount of COMT-NE and samples of unknown COMT concentration are added. The color developed from the standard COMT wells allows the unknown concentrations of COMT in the remaining wells to be determined. The procedure for carrying out the assay is illustrated in FIG. 2. Color intensity developed is inversely proportional to the COMT protein concentration in samples. (FIG. 3).

In some embodiments, the method for qualitative or quantitative detection of catechol-O-methyltransferase (COMT) in a sample, comprises:

a) providing a coated surface with a pre-determined amount of anti-COMT antibody;

b) contacting a sample with the coated surface, for binding COMT, if present in the sample, to the coated surface;

c) contacting a pre-determined amount of detectably labeled standard recombinant COMT-NE conjugate (S-COMT-NE) with the coated surface, for binding to the coated surface;

d) contacting an anti-NE antibody to the coated surface, wherein the anti-NE antibody binds to the NE epitope on the S-COMT-NE when the S-COMT-NE has previously bound to the anti-COMT antibody of the coated surface;

e) contacting the coated surface with an enzyme-labeled antibody, wherein the enzyme-labeled antibody binds to the anti-NE antibody when the anti-NE antibody has previously bound to the S-COMT-NE that is bound to the anti-COMT antibody;

f) contacting the coated surface with a chemical enzyme label indicator which indicates the presence of the enzyme labeled antibody bound to the coated surface; and g) determining the presence of COMT in the sample, or amount of COMT present in the sample, based on the presence or amount of enzyme labeled antibody bound to the coated surface.

As COMT protein levels can be altered by COMT inducers and inhibitors, and other compounds, such as xenoestrogens, PCBs, and plasticisers (Ho et al., 2008a,b), this invention can be used to measure the effects of such compounds in a rapid and simple manner.

The methods of the invention can be carried out using a diagnostic kit for qualitatively or quantitatively detecting COMT in a sample. By way of example, the kit can contain binding agents (e.g., antibodies) specific for COMT. The kit can also contain one or more other components, such as a solid support such as microtiter multi-well plates, standards, assay diluent, wash buffer, adhesive plate covers, and/or instructions (e.g., a printed document or embossed) for carrying out a method of the invention using the kit. In certain embodiments, the kit includes anti-NE and/or COMT-NE, and instructions for use of anti-NE and/or COMT-NE.

Kits of the invention may also include reagents for use in the methods described herein, in one or more containers. The kits may include specific internal controls, and/or probes, buffers, and/or excipients, separately or in combination. Each reagent can be supplied in a solid form or liquid buffer that is suitable for inventory storage. Kits may also include means for obtaining a sample from, for example, a host organism or an environmental sample.

The invention provides a simple, accurate, inexpensive, and rapid method for assaying COMT protein levels in samples of interest such as biological cultures, tissue extracts, biological fluids, and environmental samples. Current methods of measuring human COMT concentration involve laborious polyacrylamide electrophoretic/Western blotting assays and radioenzymatic assays. This novel ELISA assay will replace these existing complex and time-consuming methods.

EXAMPLE 1

Design and Preparation of Immunizing Peptide (Novel Epitope, NE)

1. A random 18-amino acid peptide sequence was generated, starting at the amino terminus with "Tyrosine (Tyr)" and consisting of the 10 hydrophilic amino acids, listed as Threonine (Thr), Serine (Ser), Aspartate (Asp), Asparagine (Asn), Glutamate (Glu), Glutamine (GM), Arginine (Arg), Lysine (Lys), Tyrosine (Tyr), Proline (Pro).
2. A computer-based search using a publically available program (BLAST) was carried out to ensure that the peptide sequences that were generated possessed no homology (at least <30%) to any human proteins.
3. The potential secondary structure of the peptide was predicted using the computer program "HNN Secondary Structure Prediction Method" (Institut de Biologie et Chimie des Protéines, France) to find a peptide which has the least ordered secondary structure (FIG. 4). An 18-mer having the following sequence was chosen: "TKENPRSN-QEESYDDNES" (SEQ ID NO: 1).
4. A peptide with the designed sequence was synthesized and purified by "Alta Bioscience, United Kingdom", for immunization to generate and purify a specific antibody, and was named NE (Novel Epitope).
5. The cDNA sequence corresponding to NE was genetically conjugated into a target human COMT gene in a protein expression vector either in a eukaryotic or bacteria system.

EXAMPLE 2

COMT and NE Antibody Production i. Immunization of Animal for NE Antibody

NE antibody was raised in animals (e.g. New Zealand Rabbit) against full length novel synthetic epitope (NE). These epitopes were chosen using hydrophilicity analysis of the protein as described (Kyte and Doolittle, 1982). Animals were injected with this antigenic polylysine peptide plus Freund's adjuvant using a multi-sited injection protocol. Whole blood samples were taken from the animal 6 weeks after the initial immunization and tested for the presence of NE antibodies. Injections were repeated at the monthly intervals until the putative antibodies were produced.

ii. Immunization and Affinity Purification of a Human COMT Antibody

COMT antibody was raised in animal (e.g. sheep) against a linear epitope of human COMT peptide as described in our previous publication (Jiang et al., 2003). The oligopeptide corresponding to residues 80-98 (DTYCEQKEWAMN-VGDKKGK) (SEQ ID NO: 7), which is common to both MB- and S-isoforms of COMT, was chosen using the hydrophilicity plot of the protein (Kyte and Doolittle, 1982).

1. The sheep was injected with this antigenic peptide on a lysine web plus Freund's adjuvant using a multisite injection protocol.
2. Whole blood samples were taken from the sheep 2 months after the initial immunization and tested for the presence of COMT antibody using the linear antigenic peptide as reference antigen in a single radial immunodiffusion assay. Injections were repeated at monthly intervals until antibodies were produced.
3. After collecting the antiserum from the animal, it was dialysed overnight with 20 mM Tris-HCl at pH 8.0 with 25 mM NaCl and 0.02% $NaN_3$. The antiserum raised was incubated with antigenic peptide on controlled pore glass beads (1 ml) for 1 hour at room temperature under constant agitation.
4. The beads and antiserum were poured into a small chromatography column (5 ml). After draining the fluid from the beads, the column was eluted with phosphate-buffered saline at pH 5.3 (100 ml) until no protein could be detected in the eluate.
5. Finally, the column was eluted with 10×1 ml aliquots of 0.1 M glycine buffer at pH 2.3. Each milliliter of eluate was brought to pH 7 immediately, and fractions with the highest protein concentration were pooled.

iii. NE Antibody Extraction And Purification

1. After collecting the antiserum from the animal, it was dialysed overnight with 20 mM Tris-HCl at pH 8.0 with 25 mM NaCl and 0.02% $NaN_3$. The dialysed antisera were loaded into the DEAE column, the size of each column was 5 times that of the serum volume. The DEAE column was washed by 3 bed volumes of 20 mM Tris-HCl, pH 8.0, 25 mM NaCl and 0.02% NaN3. The IgG peak (first peak at 280 nm absorbance to emerge from the column) was collected.

2. Aliquots of the rabbit IgG (10 ml) were incubated with antigenic peptide synthesized on controlled pore glass beads (1 ml) for 1 hour (hr) at room temperature under constant agitation.

3. The beads and the rabbit IgG were poured into a small column (5 ml). After draining all the fluid from the beads, the beads were washed with PBS at pH 7.0 (100 ml) until the UV absorption (280 nm) of the eluent was similar to that of PBS.

4. Finally, the column was eluted with 10×1 ml aliquots of 0.1M glycine at pH 2.5. Each of the eluted fractions was brought to pH 7.0 by 1M Tris immediately. The fractions containing the highest protein concentrations were pooled.

iv. Characterization of NE Antibody

The characterization of the antibody was achieved in two ways. Firstly, the antibody was raised in a rabbit and therefore initially it was present in serum with all the other antibodies that the animal had developed over its lifetime. The antibody was purified from this highly complex mixture of antibodies by its ability to bind to the NE antigen attached to control pore glass beads as described in the immediately preceding section. This binding to the antigen occurs with exhaustive elution which removes other serum proteins including other non-NE antibodies.

Figure 5:
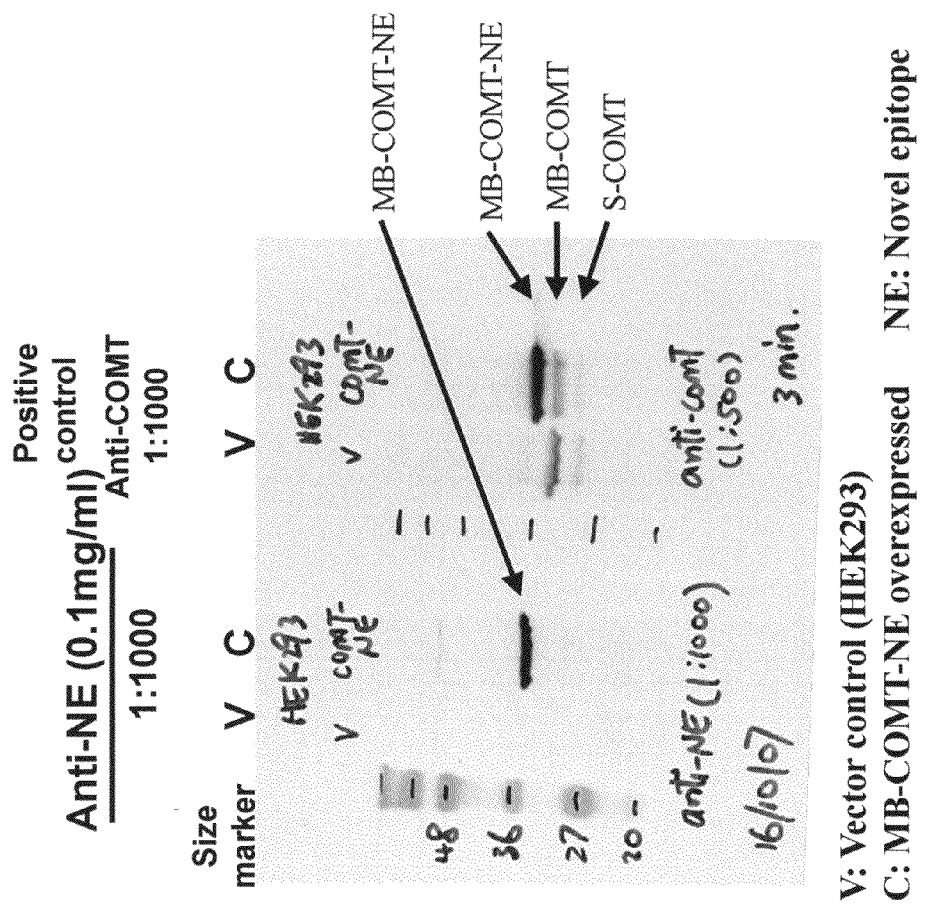
FIG. 5 shows detection of recombinant MB-COMT-NE protein in HEK293 cells by anti-NE and anti-COMT antibodies.

Secondly, the purified antibody was tested by SDS-PAGE/Western blotting. Extracts from two types of HEK293 cells were subjected to SDS-PAGE/Western blotting using the purified anti-NE as the primary detection antibody. The first type of HEK293 cell was wild-type that is generally available. These cells readily express COMT protein which is easily detectable by an anti-COMT antibody used as the primary antibody in SDS-PAGE/Western blotting (Jiang et al., 2003). The second type of HEK293 cell had been genetically engineered to express COMT-NE protein. When the purified anti-NE was used as the primary detection antibody, only COMT-NE protein was detected on the Western blot and not COMT or any other protein present in normal HEK293 extracts (FIG. 5).

Figure 6:
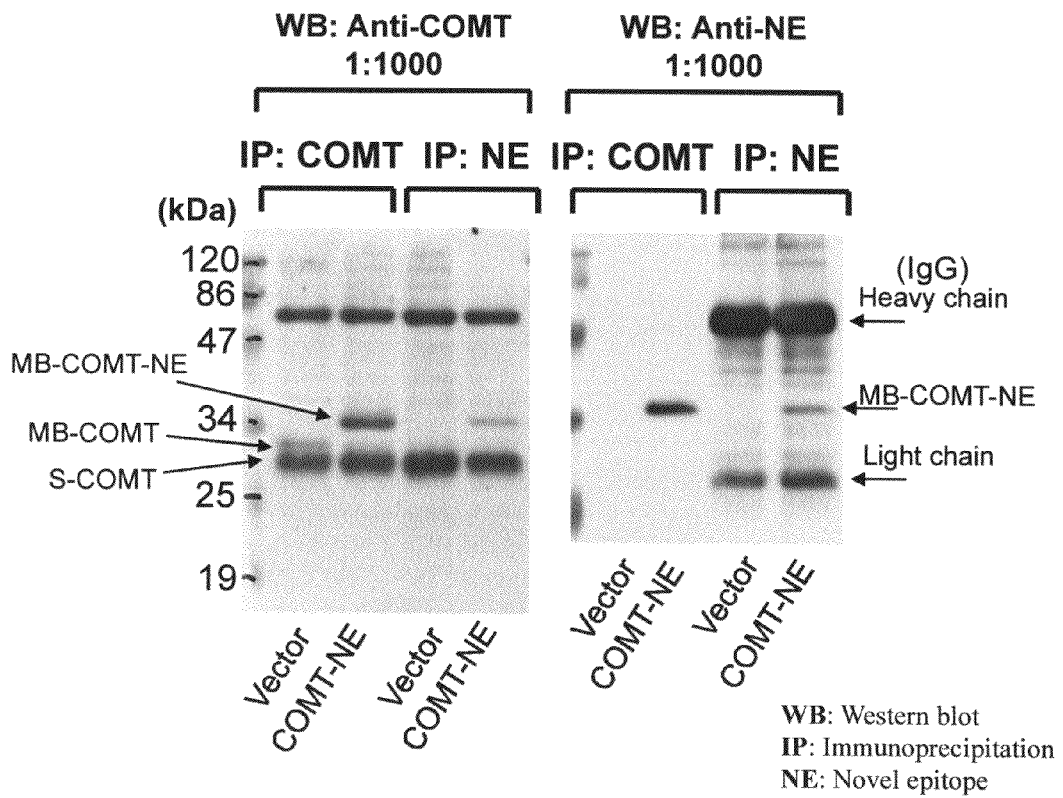
FIG. 6 shows results of immunoprecipitation (IP) and detection of recombinant MB-COMT-NE protein in HEK293 cells by anti-NE and anti-COMT antibodies.

The specificity of NE antibody was assessed by cross-detection of COMT and NE epitopes after immunoadsorption. The protein bound by anti-COMT antibody linked to sepharose protein G cross-reacted with anti-NE and vice versa. The total cell lysate from HEK293 cells overexpressing COMT-NE was incubated with COMT antibody to form an immuno-complex at 4° C. overnight to capture both the endogenous COMT and COMT-NE protein. Lysate from wild-type HEK293 cells without COMT-NE expression was done in parallel as a negative control. When this COMT-NE protein was desorbed from the sepharose protein G-anti-COMT, it cross-reacted with anti-NE when subjected to analysis using SDS-PAGE/Western blotting. (FIG. 6).

Finally, when rabbit antibodies from a rabbit that had not been immunized with NE antigen were used as the primary detection antibodies in SDS-PAGE/Western blotting no bands were detected using normal HEK293 or genetically engineered HEK293 extracts.

Thus, the purified rabbit antibody only detects COMT-NE when exposed to all the proteins present in HEK293 cell extracts and only antibodies from a rabbit immunized with NE antigen, as described above, are capable of detecting COMT protein engineered to possess the NE.

EXAMPLE 3

Preparation of Human COMT-NE Recombinant Protein

1. COMT refers to both full length of S-COMT and MB-COMT;
2. COMT-epitope refers to the 19-amino acid fragment (SEQ ID NO: 7) recognized by anti-COMT antibody.

i. Molecular Cloning of Full Length Human COMT-NE

A full length human COMT cDNA was generated from total RNA isolated from a human neuroblastoma SH-SYSY cell line (CRL-2266; American Type Culture Collection (ATCC)) by one-step RT-PCR (Titan One Tube RT-PCR Kit, Roche) according to the manufacturer's protocol, using a pair of primers specifically designed for addition of an NE cDNA fragment at the 3'-end of human COMT.

To generate a BamHI-COMT-NE-EcoRI cDNA fragment for directional cloning into the expression plasmid (pcDNA3.1(+); Invitrogen or pGEX-6p1; GE Healthcare), restricted enzyme sites (BamHI and EcoRI) were inserted by a second PCR using forward primer for human S-COMT containing a BamHI restriction site (5'-CGCGGATCCGC-CACCATGGGTGACACCAAGGAGCAGCGC-3') (SEQ ID NO: 2); or forward primer for human MB-COMT (5'-CGCGGATCCGCCACCATGCCGGAGGC-CCCGCCTCTGC-3') (SEQ ID NO: 3); and reverse primer containing the NE sequence and EcoRI restriction site (5'-CTGGAATTCTCAGCTTTCGTTATCAT-CATAGCTTTCTTCCTGGTTGCTACGCGGGT TTTCTTTGGTGGGCCCTGCTTCGCTGCCTGGGC-3') (SEQ ID NO: 4).

The COMT DNA insert (BamHI-COMT-NE-EcoRI) and empty vector (pcDNA3.1(+) or pGEX-6p1) were digested separately by excess restriction enzymes (BamHI and EcoRI) for 1 hr at 37° C. After that the digested mixtures were analyzed by 1.3% agarose gel electrophoresis at 100V for 1 hr. The resulting fragment corresponding to COMT-NE was excised and purified (Gel Extraction Kit, Viogene), and ligated to the pcDNA3.1(+) or pGEX-6p1 vector using T4 DNA ligase. The ligation reaction was incubated at 4° C. overnight.

ii. Molecular Cloning of COMT-Epitope-NE

The COMT-epitope-NE insert (BamHI-COMT-epitope-NE-EcoRI) for directional cloning into the expression plasmid (pGEX-6p1; GE Healthcare) was generated by PCR from human COMT cDNA from total RNA isolated from a human neuroblastoma SH-SYSY cell line. Restricted enzyme sites (BamHI and EcoRI) were inserted by a second PCR using forward primer for COMT-epitope containing a BamHI restriction site (5'-CGCGGATCCAGCGTGCTG-GAGGCCATTGAC-3') (SEQ ID NO: 5); and reverse primer containing the NE sequence and EcoRI restriction site (5'-CTGGAATTCTCAGCTTTCGTTATCAT-CATAGCTTTCTTCCTGGTTGCTACGCGGGT TTTCTTTGGTAATCACGGCGTCCACGATCTTGCC-3') (SEQ ID NO: 6). The COMT-epitope corresponds to residues 80-98 (DTYCEQKEWAMNVGDKKGK) (SEQ ID NO: 7) of human COMT, which is common to both MB- and S-isoforms. Ideally, the NE-epitope-"TKENPRSNQEESYDD-NES" (SEQ ID NO: 1) is used, but optionally, variants may be used so long as anti-NE-epitope will still bind the variants. Such variants can be generated by means well-known in the art, and are characterized by conservative amino acid substitutions that do not specifically change the antigenic characteristics of the 18-mer. For example, amino acids that either occur infrequently or never in proteins and peptides and synthetic amino acids can be substituted for the amino acids of NE-epitope, so long as the NE-epitope having the substituted amino acids retains substantially the same antigenic characteristics as the NE-epitope in which amino acids have not been substituted. Examples of amino acids that either occur infrequently or never in proteins and peptides and synthetic amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Amino acids that either occur infrequently or never in proteins and peptides and synthetic amino acids also include amino acids having derivatized side groups. Furthermore, any of the amino acids in the protein can be of the D (dextrorotary) form or L (levorotary) form. Allelic variants of a protein sequence of NE-epitope of the present invention are also encompassed within the scope of the invention.

Amino acids can be generally categorized in the following classes: non-polar, uncharged polar, basic, and acidic. Conservative substitutions whereby a NE-epitope of the present invention having an amino acid of one class is replaced with another amino acid of the same class fall within the scope of the subject invention so long as the NE-epitope having the substitution still retains substantially the same antigenic characteristics (e.g. binding to anti-NE-epitope) as the NE-epitope that does not have the substitution. Isolated polynucleotides encoding a NE-epitope having one or more amino acid substitutions in the sequence are contemplated within the scope of the present invention. In one embodiment, the isolated polynucleotide encoding a variant of NE-epitope comprises a nucleic acid sequence which hybridizes under stringent conditions to a nucleic acid sequence encoding the NE-epitope and encodes a variant of NE-epitope that binds with antibody to NE-epitope.

Table 1 below provides a listing of examples of amino acids belonging to each class.

TABLE 1

| Class of Amino Acid | Examples of Amino Acids |
| --- | --- |
| Non-polar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Variants having substantial identity or homology with the polypeptide "NE-epitope" or polynucleotides encoding the NE-epitope may be utilized in the practice of the invention. Such sequences can be referred to as variants or modified sequences. That is, a polynucleotide sequence may be modified yet still retain the ability to encode a polypeptide exhibiting the desired antigenic characteristics, for example, ability to bind with antibody to NE. Such variants are thus functional equivalents. Generally, the variant will comprise at least about 60%-80%, preferably about 80%-90%, and even more preferably about 90%-95% sequence identity with the native sequence. Optionally the variant can be derived from NE-epitope by substitution, deletion or addition of one or several amino acids in the amino acid sequence. Three novel peptide variants are designed with modified NE sequences containing the following sequences: "TKENPRTNQEESYDDNES" (SEQ ID NO: 8), "TKENPRSNQDESYDDNES" (SEQ ID NO: 9), and "TKENPRSNQPPSYDDNES" (SEQ ID NO: 10). The immuno-reactivity against NE-antibody of these three modified NE sequences (SEQ ID NO: 8-10) were tested as examples.

Sequence relationships between two or more nucleic acids or polynucleotides are generally defined as sequence identity, percentage of sequence identity, and substantial identity. In determining sequence identity, a "reference sequence" is used as a basis for sequence comparison. The reference may be a subset or the entirety of a specified sequence. That is, the reference sequence may be a full-length gene sequence or a segment of the gene sequence.

Methods for alignment of sequences for comparison are well known in the art. See, for example, Smith et al. (1981) *Adv. Appl. Math.* 2:482; Needleman et al. (1970) *J. Mol. Biol.* 48:443; Pearson et al. (1988) *Proc. Natl. Acad. Sci.* 85:2444; CLUSTAL in the PC/Gene Program by Intelligenetics, Mountain View, Calif.; GAP, BESTFIT, BLAST, FASTA, and TFASTA in the Wisconsin Genetics Software Package, Genetics Computer Group (GCG), 575 Science Drive, Madison, Wis., USA. Preferred computer alignment methods also include the BLASTP, BLASTN, and BLASTX algorithms. See, Altschul et al. (1990) *J. Mol. Biol.* 215:403-410.

"Sequence identity" or "identity" in the context of nucleic acid or polypeptide sequences refers to the nucleic acid bases or residues in the two sequences that are the same when aligned for maximum correspondence over a specified comparison window. "Percentage of sequence identity" refers to the value determined by comparing two optimally aligned sequences over a comparison window, wherein the portion of the polynucleotide sequence in the comparison window may comprise additions or deletions as compared to the reference window for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Polynucleotide sequences having "substantial identity" are those sequences having at least about 50%-60% sequence identity, generally at least 70% sequence identity, preferably at least 80%, more preferably at least 90%, and most preferably at least 95%, compared to a reference sequence using one of the alignment programs described above. Preferably, sequence identity is determined using the default parameters determined by the program. Substantial identity of amino acid sequence generally means sequence identity of at least 60%, more preferably at least 70%, 80%, 90%, and most preferably at least 95%.

Nucleotide sequences are generally substantially identical if the two molecules hybridize to each other under stringent conditions. Generally, stringent conditions are selected to be about 5° C. lower than the thermal melting point for the specific sequence at a defined ionic strength and pH. Nucleic acid molecules that do not hybridize to each other under stringent conditions may still be substantially identical if the polypeptides they encode are substantially identical. This may occur, for example, when a copy of a nucleic acid is created using the maximum codon degeneracy permitted by the genetic code.

As noted, hybridization of sequences may be carried out under stringent conditions. By "stringent conditions" is intended conditions under which a probe will hybridize to its target sequence to a detectably greater degree than to other sequences. Stringent conditions are sequence-dependent and will be different in different circumstances. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary stringent conditions include hybridization with a buffer solution of 30 to 35% formamide, 1.0 M NaCl, 1% SDS (sodium dodecyl sulphate) at 37° C., and a wash in 1× to 2×SSC (20×SSC=3.0 M NaCl/0.3 M trisodium citrate) at 50 to 55° C. It is recognized that the temperature, salt, and wash conditions may be altered to increase or decrease stringency conditions. For the post-hybridization washes, important factors include the ionic strength and temperature of the final wash solution. See, Meinkoth and Wahl (1984) *Anal. Biochem.* 138:267-284.

EXAMPLE 4

Transformation of the Recombinant Plasmid

The recombinant product from the ligation reaction was transformed into chemically competent *E. Coli* cells (BL21). The details procedures are as described:
1. Competent cells (100 µl) stored in the −70° C. freezer were placed on ice for 5 min.
2. An aliquot of the ligation solution (2-5 µl) was added to the competent cells (100 µl), and the whole mixture was swirled gently several times and stored on ice for 30 min. The tube was then transferred to a rack placed in a circulating water bath pre-heated to 42° C. and left for 45 seconds. Care was taken not to shake the tubes.
3. The tubes were rapidly transferred to an ice bath and chilled for 2 min. SOC medium (500 µl) was added to each tube. The tubes were transferred to a shaking incubator (225 rpm/min) and incubated at 37° C. for 1 hr to allow the bacteria to recover and express the antibiotic resistance maker encoded by the plasmid.
4. The appropriate volume (up to 250 µl per 90-mm plate) of transformed competent cells was transferred onto LB agar containing ampicillin (50 µg/ml) and spread onto the surface of the agar plate by a sterile bent glass rod.
5. The plate was inverted and incubated at 37° C. Colonies appeared in 12-18 hr.

EXAMPLE 5

Identification of Bacterial Colonies Containing Recombinant Plasmids

At least 10 individual colonies were picked and plasmid DNA was extracted by Mini-prep purification kit (Qiagen™). Plasmid was digested with BamHI and EcoRI and visualized in 1.3% agarose gel at 100V for 45 minutes. The resulting plasmid DNA containing the correct COMT-NE or COMT-epitope-NE insert was verified by sequencing.

EXAMPLE 6

Bacterial Expression of Recombinant Human COMT-NE

Figure 7:
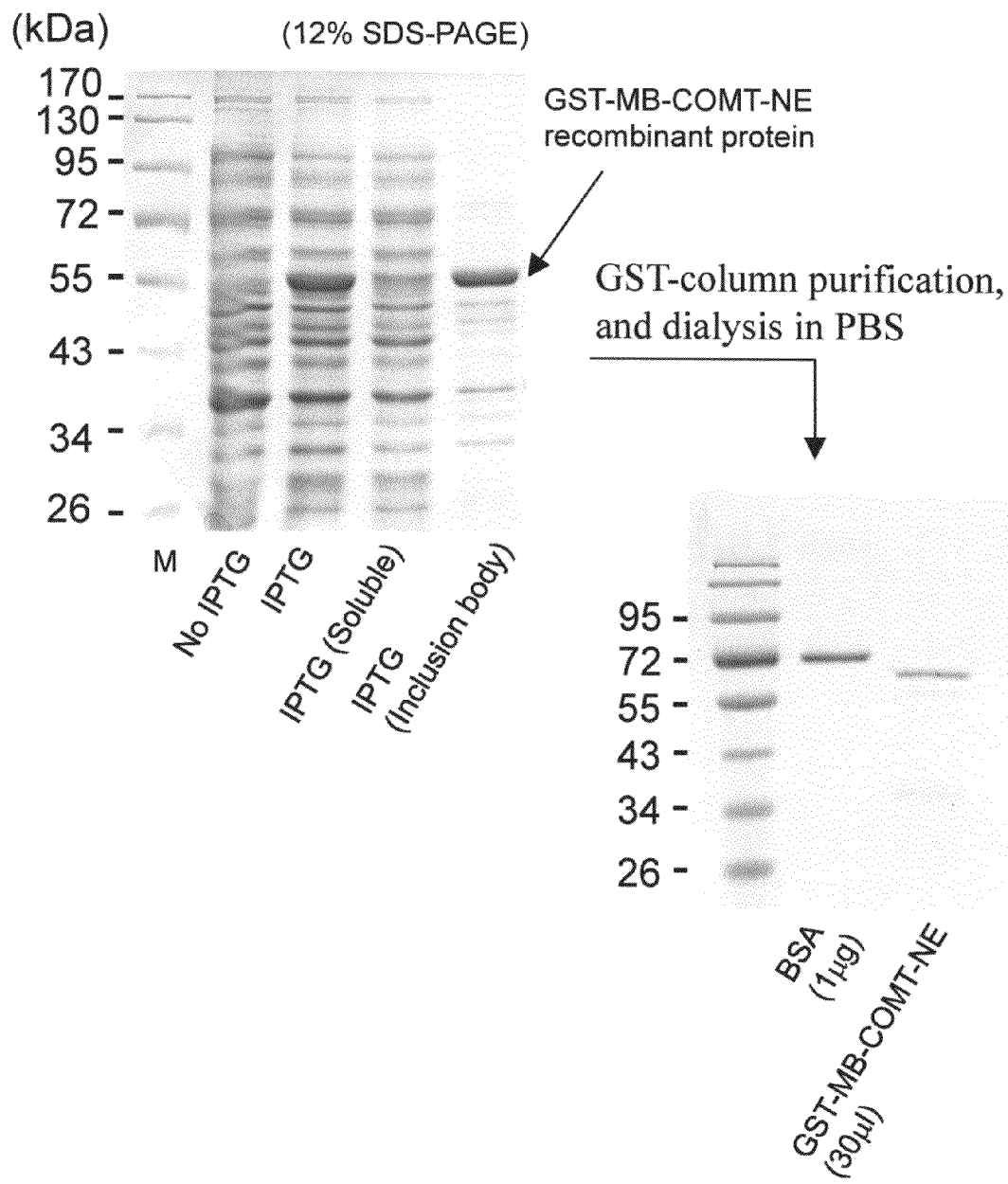
FIG. 7 shows Coomassie blue protein staining of recombinant MB-COMT-NE protein in *Escherichia coli*.
Figure 8:
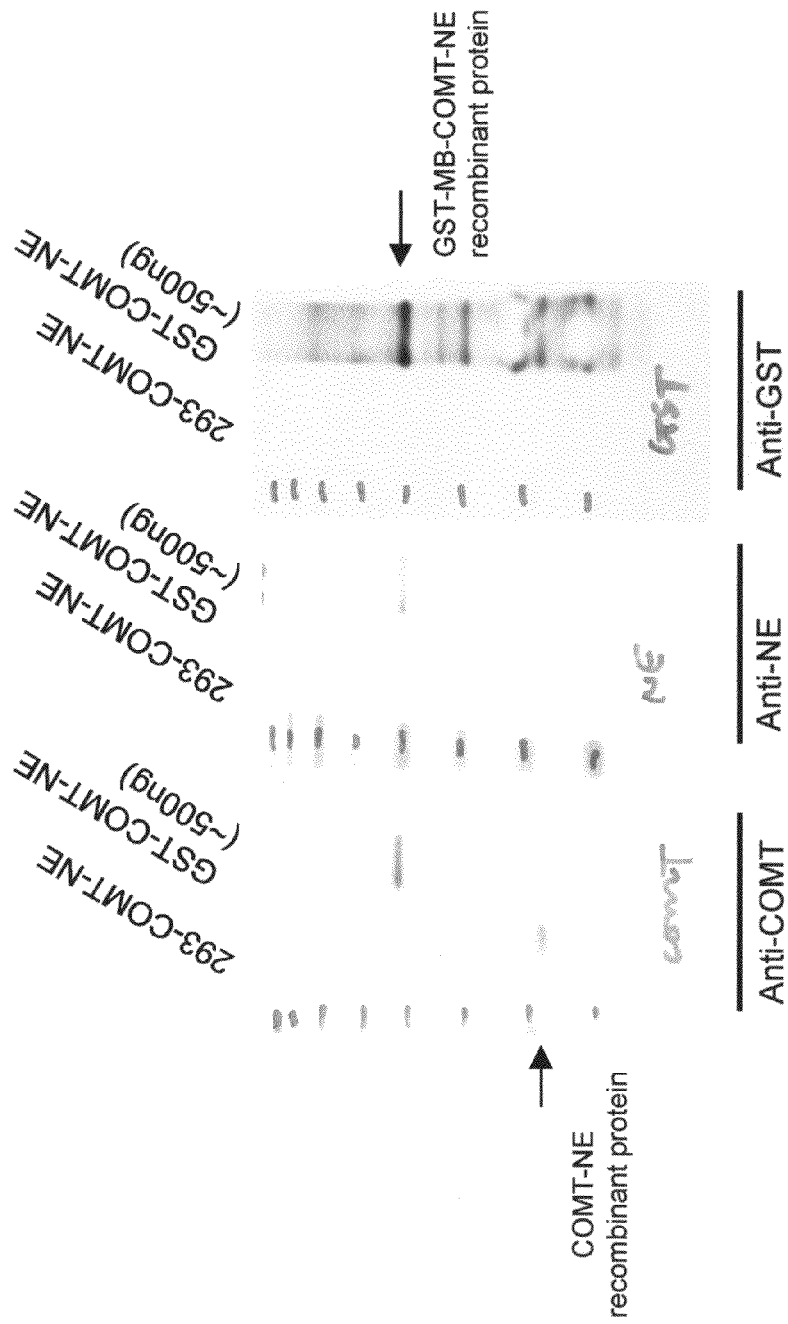
FIG. 8 shows detection of recombinant GST-MB-COMT-NE protein by anti-NE, anti-COMT and anti-GST antibodies.
Figure 9:
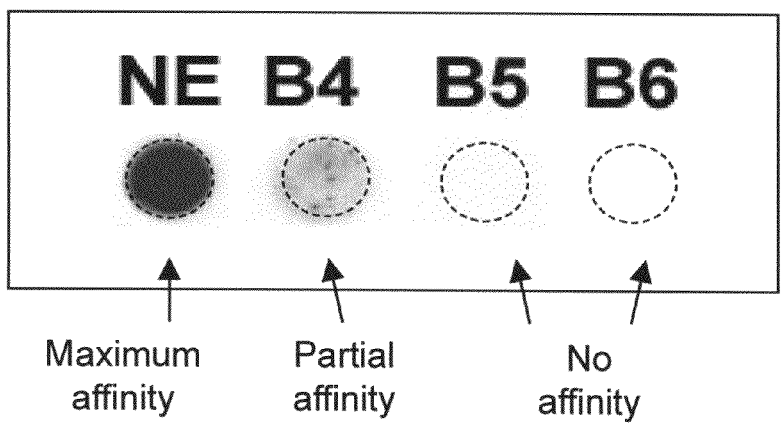
FIG. 9 shows the results of a dot-blot assay to determine affinity binding on modified NE epitopes by anti-NE antibody. Also shown is a table with examples of conservative (intra-class) amino acid substitutions that may be made to produce other NE-epitope variants potentially having substantially the same antigenic characteristics (e.g., binding to anti-NE-epitope).

For expression of recombinant human COMT-NE protein in *E. coli* (BL21), a positive clone was culture in LB broth supplemented with ampicillin (50 µg/ml) and incubated at 37° C. with vigorous shaking until the optical density reading of the bacterial culture reached ~0.6 (at λ=600 nm). The culture was induced with isopropylthio-β-D-galactoside (at a final concentration of 0.1-1 mM) and cultured for another 4 hr. Cells were collected by centrifugation and were sonicated in ice-cold lysis buffer (50 mM Tris-Cl, pH 7.5, 200 mM NaCl), supplemented with 5 mM 1,4-dithiothreitol (DTT) and 1 mM phenylmethylsulfonyl fluoride (PMSF). The expressed COMT-NE or COMT-epitope-NE recombinant protein from bacterial lysate was purified by passing through a commercially available glutathione-S-transferase (GST)-purification column (GSTrap™ FF, GE Healthcare). The target protein band was visualized in SDS-PAGE after Coomassie blue staining, and characterized by Western blot (FIGS. 7 and 8).

EXAMPLE 7

Determination of Non-Specific Binding Affinity on Modified NE-Epitope by Anti-NE Antibody Variants having substantial homology with the polypeptide "NE-epitope" or polynucleotides encoding the NE-epitope may be utilized in the practice of the invention. That is, a polynucleotide sequence may be modified yet still retain the ability to encode a polypeptide exhibiting the desired antigenic characteristic of binding to NE-antibody. The immunoreactivity against NE-antibody of three modified NE sequences (SEQ ID NO: 8-10) were tested by dot-blotting as examples.

The procedure for carrying out the dot-blot assay is described as followed and the results are illustrated in FIG. 9.

1. Peptides comprising modified NE sequences were synthesized and purified by a commercial company. (Alta Bioscience, Birmingham UK)
2. 10 ng of each of the peptide were dissolved in PBS and spotted onto a nitrocellulose membrane using a narrow-mouth pipette tip. The membrane was air-dried.
3. The membrane was blocked by 5% BSA in TBS-T for 1 hr, and then incubated with anti-NE antibody diluted in BSA/TBS-T for 2 hr at room temperature.
4. After incubation, the membrane was washed three times with TBS-T, and then incubated with secondary antibody conjugated with HRP (anti-rabbit; DAKO) for 1 hr at room temperature.
5. The membrane was washed for three times with TBS-T, and incubated with ECL reagent for 1 min.
6. The membrane was exposed to X-ray film in the dark room and signal from different samples were compared. The intensity of the signal was proportional to the level of binding affinity of each peptide against anti-NE antibody.

From the results illustrated in FIG. 9, the NE peptide demonstrated strong binding affinity against anti-NE antibody. One of the three modified NE peptides (SEQ ID NO. 8) demonstrated binding with NE antibody (although with lower affinity than NE), but the other two peptides (SEQ ID NO. 9, 10) do not retain significant immuno-reactivity against NE antibody (FIG. 9).

EXAMPLE 8

Construction of the COMT Enzyme Immunoassay (EIA) System

Two unique antibodies (anti-COMT and anti-NE), two proteins (COMT and COMT-NE) and an artificially constructed peptide "COMT-epitope-NE", are produced. The novel synthetic epitope (NE) consists of 18 amino acids with the following sequence: "TKENPRSNQEESYDDNES" (SEQ ID NO: 1), and serves as a tag for detection of target protein.

The COMT antibody was raised and affinity purified as described in EXAMPLE 2 above.

Various chemicals for washing and color formation and a third antibody (anti-anti-NE or anti-rabbit IgG antibody) with an enzyme conjugated to the antibody are purchased from any number of suppliers. These are commonly available.

The assay requires wells in a plastic plate containing 96 wells be coated with a predetermined fixed amount of anti-COMT bound to the bottom of each well.

In eight of the wells predetermined fixed amounts of COMT and a fixed amount of COMT-NE are added so that a standard curve may be generated from the results obtained from these wells. In the remaining well a fixed amount of COMT-NE and samples of unknown COMT concentration are added. The color developed from the standard COMT wells allows the unknown concentrations of COMT in the remaining wells to be determined.

The procedure for carrying out an embodiment of the COMT ELISA assay is described as follows and illustrated in FIG. 2.
1. A transparent 96-well plastic plate was coated with 0.1 µg COMT antibodies overnight at 4° C.
2. The plate was pre-blocked with 1% BSA for 1 hr at room temperature.
3. Recombinant COMT-NE standard protein with different concentrations were mixed with fixed amount of sample lysate and were added into each individual well, and incubated for 2 hr at room temperature.
4. After washes with PBS with 0.1% Tween-20, the plate was incubated with anti-NE for 2 hr at room temperature.
5. The plate was washed again and incubated with secondary antibodies (anti-rabbit; DAKO) for 1 hr at room temperature.
6. TMB substrate (TMB substrate; Pierce, #34021) was prepared at ratio of 1:1 with $H_2O_2$ for colorimetric development, and incubated for 15 min. at room temperature in the dark.
7. The color development reaction was stopped by addition of a small volume of 2M $H_2SO_4$ into each well.
8. The absorbance was measured at 450 nm by spectrophotometer. Color intensity developed is inversely proportional to the COMT concentration. (FIG. 3)

EXAMPLE 9

Application of COMT Enzyme Immunoassay (EIA) Kit

Principle of the Test

The COMT EIA Kit is a solid phase enzyme-linked immunosorbent assay (ELISA), based on the principle of competitive binding. The microtiter wells are coated with a polyclonal antibody directed towards an antigenic site on the COMT molecule. Endogenous COMT protein in sample competes with the standard recombinant COMT-NE conjugate for binding to the coated antibody. After incubation the unbound COMT-NE protein is washed off. Anti-NE is attached to the bound standard recombinant COMT-NE and excess anti-NE is washed off, and then anti-rabbit IgG conjugated with a color-producing enzyme (in this instance horseradish peroxidase) is attached to bound anti-NE and excess washed off and color developed by adding an appropriate substrate for the color-producing enzyme. The amount of bound colorogenic conjugate (in this case donkey anti-rabbit IgG conjugated with horseradish peroxidase) is inversely proportional to the concentration of COMT in the sample. After addition of the substrate solution, the intensity of color developed is inversely proportional to the concentration of COMT in the sample.

It should be understood, however, that the foregoing description is merely illustrative and that various modifications or changes in reagents may be made without changing the general principle of the assay. The ELISA methods provided herein, each include multiple steps, and the foregoing is a description of the general methodology utilized in performing those steps. The description is not to be construed as limiting the present invention, however, inasmuch as minor adjustments and/or changes in the methodology of the present invention may be made without departing from the scope of the invention disclosed herein. It is particularly noted that the present invention is construed to include those instances in which one skilled in the art may utilize different but equivalent substrate types, animal antibody types, enzyme labels, enzyme label indicators, coating solutions, blocking solutions and wash solutions, to those disclosed herein. For example, it should be noted that the species in which the three antibodies used here are raised are not critical. The principle of the assay relies on the fact that the three antibodies do not cross-react. This is most easily achieved by using three different species, (in this case sheep, rabbit and donkey). Antibodies against the three antigens (COMT, NE and anti NE immunoglobulin) raised in other species could be used equally well. It should also be noted that the color-producing enzyme and substrate can be replaced by other such enzymes and substrates. Furthermore, it should be noted that other systems for detecting the amount of anti-NE bound to the captured COMT-NE can replace the color development system described herein (e.g., use of fluorescence, or luminescence). It should also be noted that a color-producing enzyme or other detection system for detecting the amount of anti-NE bound to the captured COMT-NE can be conjugated directly to the anti-NE.

Materials:
1. Sample protein (MCF-7 cells)
2. Competitor protein (S-COMT-NE, 1 mg/ml)
3. Standard protein (S-COMT-FLAG, 1 mg/ml)
4. Detection antibody (Rabbit anti-NE antibody)
5. Sheep anti-Rabbit IgG-HRP
6. TMB substrate & Stop solution
7. Sample diluent
8. Wash solution
9. 96-well plates Sample Extraction Procedure:

MCF-7 (HTB-22) cells were obtained from American Type Culture Collection (ATCC), which express S-COMT almost exclusively. Cells were grown in Dulbecco's Modified Eagle Medium (DMEM) containing 10% heat-inactivated fetal bovine serum, antibiotics (100 U/ml of penicillin and 100 m/ml of streptomycin), and 1 µg/ml insulin in humidified 5% $CO_2$ at 37° C. The cells (0.5 ml; containing approximately $1 \times 10^6$ cells) were detached from the surface of the culture dish, plate, or well by exposure to trypsin followed by the addition of fresh medium (0.8 ml). The cell suspension was then transferred into a 1.5 ml centrifuge tube. The tube was centrifuged at 1,300 r.p.m. for 5 min. and the supernatant discarded. The cell pellet was re-suspended and washed with 0.5 ml PBS, and re-centrifuge at 1,300 r.p.m. for 5 min. The supernatant was discarded and ice-cooled double-distilled water (0.2 ml) was added to resuspend the cell pellet. The cell suspension was ultrasonicated for 10 sec. on ice. The lysate was centrifuged at 14,000 r.p.m. at 4° C. for 15 min. The supernatant was transferred to a new 1.5 ml centrifuge tube, to determine the total protein concentration, and then stored in −70° C. before use.

Test Procedure:

Each run preferably includes a standard curve. Desired number of antibody-coated microtiter wells in the rack was determined. The plate was blocked by adding 200 µl of 1% BSA in PBS in each well and incubated at room temperature for 1 hr. Competitor (S-COMT-NE) was diluted with sample diluent to make a 10 µg/ml concentration. A serial dilution of standard reaction mix (Competitor+Standard) 100 µl of each with new disposable tips into appropriate wells was prepared as summarized in Table 2.

TABLE 2

| | +Competitor (S-COMT-NE, 10 µg/ml) | | | | | |
|---|---|---|---|---|---|---|
| Standard | 80 µg/ml | 40 µg/ml | 20 µg/ml | 10 µg/ml | 5 µg/ml | 2.5 µg/ml | 0 µg/ml |

Protein samples (e.g. MCF-7 total lysate) in sample diluent were diluted and added to a concentration of 50 to 200 µg total protein per well (100 µl) in each appropriate well. After loading the standards and samples (100 µl each) into the appropriate wells, the plate was incubated for 2 hr at room temperature. After incubation, the contents of the wells was briskly shaked out, and the wells were rinsed for 5 times with diluted Wash Solution (200 µl per well). The wells were sharply stroked on absorbent paper to remove residual droplets. 100 µl/well of Detection antibody (Rabbit anti-NE) were added and incubated for 1 hr at room temperature. The contents of the wells were shaken out and washed thoroughly for 5 times. Then, 100 µl/well of anti-rabbit IgG-HRP were added in each well, and incubated for 1 hr at room temperature. The contents of the wells were shaken out and washed thoroughly for 5 times again. For colorimetric development, 100 µl of substrate solution were added to each well by mixing equal volumes of TMB substrate, and incubated for 15 to 30 min. at room temperature or until the desired color develops. The enzymatic reaction was stopped by adding 100 µl of Stop Solution to each well. The optical density (OD) at 450±10 nm with a microtiter plate reader was recorded within 10 minutes after adding the Stop Solution.

Figure 11:
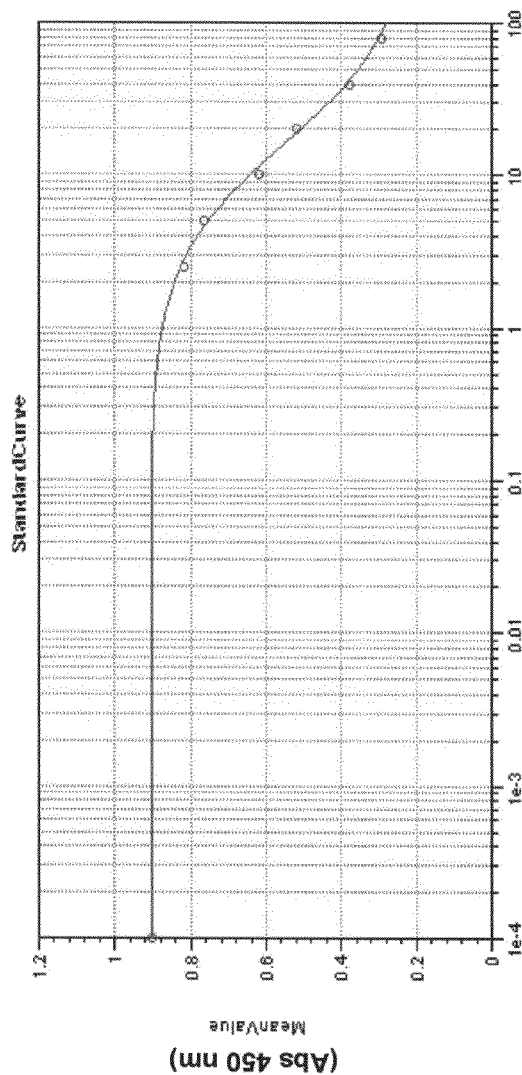
FIG. 11 shows an example of a standard curve of a COMT EIA kit.

Plot Calibration Curve:

The calibration curve is obtained by plotting the Standard (S-COMT-FLAG) concentration on the log scale against the $OD_{450}$ on the linear scale for each calibrator. Validated statistical software can be used to generate standard curve that best fits the data. (FIG. 11)

Sample Analysis:

Substitute experimental samples for the COMT standard but ensuring that the total sample volume is equivalent to that used to generate the standard curve. Calculate the amount of COMT in experimental samples from the standard curve. Table 3 below listed the calculated COMT concentration in each of four protein samples from COMT EIA kit in terms of micro-gram (µg) COMT per milli-gram (mg) total cellular protein.

TABLE 3

| Samples (total protein in µg) | mean Abs. | standard deviation | Calculated COMT conc. | COMT per mg total cellular protein |
|---|---|---|---|---|
| Sample #1 (200 µg) | 0.7845 | 0.0344 | 3.9188 | 19.59 µg/mg protein |
| Sample #2 (100 µg) | 0.8475 | 0.0303 | 1.8393 | 18.39 µg/mg protein |
| Sample #3 (50 µg) | 0.8955 | 0.0274 | 1.0515 | 21.03 µg/mg protein |
| Sample #4 (25 µg) | 0.8970 | 0.0104 | 0.3118 | 12.47 µg/mg protein |

CONCLUSION

Protein samples (MCF-7 cell lysate) between 50 to 200 µg per well gave OD readings within the dynamic range of the standard curve. The COMT concentration in protein samples can be acquired from the formula generated according to the standard curve. The level of COMT is expressed as microgram (µg) COMT per milli-gram (mg) total cellular protein.

Figure 10:
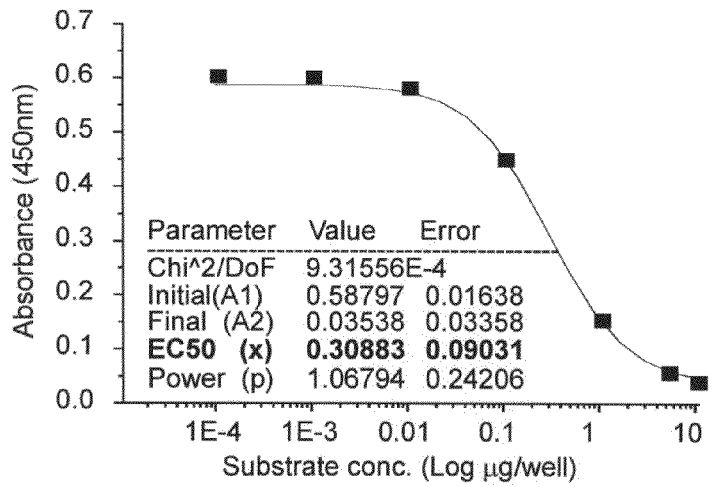
FIG. 10 shows an example of COMT competitive ELISA assay in MCF-7 cell lysate.
Figure 10:
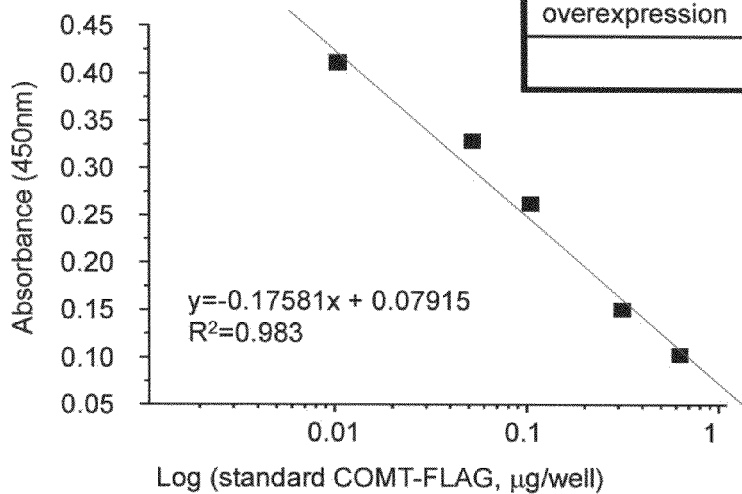

Thus the use of a human cell culture system and the COMT assay described here can form an effective screening system for estrogen-mimetics which pose a wide range of human health and environmental hazards. An example of COMT competitive ELISA assay is demonstrated in FIG. 10. Briefly, the human MCF-7 cells were treated with 17β-estradiol for 48 hr. The total cell lysate was collected and the level of COMT protein expression was determined by COMT competitive ELISA assay. The results showed that COMT protein level in MCF-7 cells was decreased after exposure to 17β-estradiol compared with the untreated control. Lysate from HEK293 cells overexpressing COMT-NE was used as a positive control in this assay, which showed an increase in COMT protein level compared with the control.

All patents, patent applications, provisional applications, and publications referred to or cited herein are incorporated by reference in their entirety, including all figures and tables, to the extent they are not inconsistent with the explicit description of this specification.

It should be understood that the examples and embodiments described herein are for illustrative purposes only and that various modifications or changes in light thereof will be suggested to persons skilled in the art and are to be included within the spirit and purview of this application.

REFERENCES

Bonifácio M J, Palma P N, Almeida L, Soares-da-Silva P. Catechol-O-methyltransferase and its inhibitors in Parkinson's disease. *CNS Drug Rev.* 2007, 13(3):352-379. Review.

Ho P W L, Chu A C Y, Kwok K H H, Liu H F, Kung M H W, Ramsden D B, Ho S L. Effects of Plasticisers and Related Compounds on the Expression of the Soluble Form of Catechol-O-Methyltransferase in MCF-7 Cells. *Curr. Drug Metab.* 2008a, 9(4):276-9.

Ho P W L, Garner C E, Ho J W M, Leung K C, Kwok K H H, Chu A C Y, Kung M H W, Burka L T, Ramsden D B, Ho S L. Estrogenic phenol and catechol metabolites of PCBs down-regulate catechol-O-methyltransferase via the estrogen receptor: potential contribution to cancer risk. *Curr. Drug Metab.* 2008b, 9(4):304-9.

Houston M C. The role of mercury and cadmium heavy metals in vascular disease, hypertension, coronary heart disease, and myocardial infarction. *Altern. Ther. Health Med.* 2007, 13(2):S128-133.

Jiang H, Xie T, Ramsden D B, Ho S L. Human catechol-O-methyltransferase down-regulation by estradiol. *Neuropharmacology.* 2003, 45, 1011-1018.

Kyte J, Doolittle R F. A simple method for displaying the hydropathic character of a protein. *J. Mol. Biol.* 1982, 157(1):105-132.

Lewandowski K E. Relationship of catechol-O-methyltransferase to schizophrenia and its correlates: evidence for associations and complex interactions. *Harv. Rev. Psychiatry.* 2007, 15(5):233-244.

Thompson P A, Ambrosone C. Molecular epidemiology of genetic polymorphisms in estrogen metabolizing enzymes in human breast cancer. *J. Natl. Cancer Inst. Monogr.* 2000, 125-134.

Tom T, Cummings J L. Depression in Parkinson's disease. Pharmacological characteristics and treatment. *Drugs Aging.* 1998, 12(1):55-74.

Xie T, Ho S L, Ramsden D B. Characterization and implications of estrogenic down-regulation of human catechol-O-methyltransferase gene transcription. *Mol. Pharmacol.,* 1999, 56, 31-38.

What is claimed is:

1. An isolated polypeptide comprising a Novel Epitope (NE-epitope) having the sequence of SEQ ID NO: 1.

2. The polypeptide of claim 1, further comprising a catechol-O-methyltransferase (COMT)-epitope.

3. The polypeptide of claim 2, wherein the catechol-O-methyltransferase is a membrane bound catechol-O-methyltransferase.

4. The polypeptide of claim 2, wherein the catechol-O-methyltransferase is a soluble-catechol-O-methyltransferase.

5. The polypeptide of claim 2, wherein the COMT-epitope comprises SEQ ID NO:7.

6. An assay kit comprising the polypeptide of claim 1.

7. The assay kit according to claim 6, further comprising an anti-COMT antibody.

8. An assay kit comprising the polypeptide of claim 2.

9. An assay kit comprising the polypeptide of claim 3.

10. An isolated antibody that specifically binds to the amino acid sequence of SEQ ID NO:1 (anti-NE-epitope antibody).

11. An assay kit comprising the antibody of claim 1.

12. The assay kit according to claim 11, further comprising an anti-COMT antibody.

13. A method for qualitative or quantitative detection of catechol-O-methyltransferase (COMT) in a sample, comprising:
  a) providing a coated surface with a pre-determined amount of anti-COMT antibody bound to the coated surface;
  b) contacting a sample with the coated surface, for binding COMT protein, if present in the sample, to the anti-COMT antibody on the coated surface;
  c) contacting a pre-determined amount of detectably labeled COMT-Novel Epitope (COMT-NE) conjugate with the coated surface, for binding to the anti-COMT antibody on the coated surface, wherein the COMT-NE conjugate comprises a COMT protein fused with an NE-epitope, the NE-epitope having the amino acid sequence of SEQ ID NO:1;
  d) contacting an anti-NE-epitope antibody to the coated surface, wherein the anti-NE-epitope antibody binds to the amino acid sequence of SEQ ID NO:1 of the NE-epitope on the COMT-NE conjugate when the COMT-NE conjugate has previously bound to the anti-COMT antibody of the coated surface;
  e) contacting the coated surface with an enzyme-labeled antibody, wherein the enzyme-labeled antibody binds to the anti-NE-epitope antibody when the anti-NE-epitope antibody has previously bound to the COMT-NE conjugate that is bound to the anti-COMT antibody;
  f) contacting the coated surface with a chemical enzyme label indicator which indicates the presence of the enzyme labeled antibody bound to the anti-NE-epitope antibody; and
  g) determining the presence of COMT protein in the sample, or amount of COMT protein present in the sample, based on the presence or amount of enzyme labeled antibody bound to the anti-NE-epitope antibody.

* * * * *

UNITED STATES PATENT AND TRADEMARK OFFICE
CERTIFICATE OF CORRECTION

| | |
|---|---|
| PATENT NO. | : 8,927,225 B2 |
| APPLICATION NO. | : 12/555529 |
| DATED | : January 6, 2015 |
| INVENTOR(S) | : Shu Leong Ho, Wing Lok Ho and David Boyer Ramsden |

It is certified that error appears in the above-identified patent and that said Letters Patent is hereby corrected as shown below:

In the Specification

Column 7,
Line 1, "NaN3" should read --$NaN_3$--.

Column 8,
Line 12, "SH-SYSY" should read --SH-SY5Y--.
Line 48, "SH-SYSY" should read --SH-SY5Y--.

Column 11,
Line 67, "was culture in" should read --was cultured in--.

Column 12,
Line 33, "as followed" should read --as follows--.

Column 14,
Line 1, "colorogenic" should read --chlorogenic--.
Lines 56-57, "100 m/ml" should read --100 μg/ml--.

Column 15,
Line 64, "listed" should read --lists--.

Signed and Sealed this
Twentieth Day of October, 2015

Michelle K. Lee
*Director of the United States Patent and Trademark Office*